United States Patent
Phillips et al.

(10) Patent No.: US 12,144,988 B2
(45) Date of Patent: Nov. 19, 2024

(54) EEG CURVE FITTING TO SPECIFY STIMULATION PARAMETER

(71) Applicant: Wave Neuroscience, Inc., Newport Beach, CA (US)

(72) Inventors: James William Phillips, Fountain Valley, CA (US); Robert Isenhart, Orange, CA (US); Alexander Ring, Newport Beach, CA (US)

(73) Assignee: WAVE NEUROSCIENCE, INC., Newport Beach, CA (US)

(*) Notice: Subject to any disclaimer, the term of this patent is extended or adjusted under 35 U.S.C. 154(b) by 0 days.

(21) Appl. No.: 17/072,007

(22) Filed: Oct. 15, 2020

(65) Prior Publication Data

US 2021/0128917 A1 May 6, 2021

Related U.S. Application Data

(60) Provisional application No. 63/021,457, filed on May 7, 2020, provisional application No. 62/915,343, filed on Oct. 15, 2019.

(51) Int. Cl.
*A61N 1/36* (2006.01)
*A61N 1/04* (2006.01)

(52) U.S. Cl.
CPC ....... *A61N 1/36031* (2017.08); *A61N 1/0404* (2013.01); *A61N 1/36034* (2017.08)

(58) Field of Classification Search
CPC .............. A61N 1/0404; A61N 1/36023; A61N 1/36031; A61N 1/36034; A61N 2/006; A61N 2/02; A61B 5/374; A61B 5/4836
USPC ............................................................ 607/45
See application file for complete search history.

(56) References Cited

U.S. PATENT DOCUMENTS

| | | | |
|---|---|---|---|
| 6,381,559 B1 | 4/2002 | Huang | |
| 8,475,354 B2 | 7/2013 | Phillips et al. | |
| 9,308,385 B2 | 4/2016 | Jin | |
| 2011/0112427 A1* | 5/2011 | Phillips | A61B 5/407 600/9 |
| 2011/0137104 A1* | 6/2011 | Phillips | A61N 2/008 600/9 |
| 2016/0008620 A1* | 1/2016 | Stubbeman | A61N 1/36082 607/45 |
| 2018/0126184 A1 | 5/2018 | Phillips et al. | |
| 2018/0221661 A1* | 8/2018 | Choe | A61M 21/02 |
| 2019/0030336 A1* | 1/2019 | Kwan | A61N 1/36025 |
| 2019/0247650 A1* | 8/2019 | Tran | A61N 1/3704 |
| 2021/0236821 A1* | 8/2021 | Sinclair | A61B 5/4821 |
| 2021/0346710 A1* | 11/2021 | Phillips | A61N 2/006 |
| 2021/0353224 A1* | 11/2021 | Etkin | G16H 50/70 |

FOREIGN PATENT DOCUMENTS

| | | |
|---|---|---|
| WO | 2018204021 A1 | 11/2018 |
| WO | 2021076819 A1 | 4/2021 |

\* cited by examiner

*Primary Examiner* — Carl H Layno
*Assistant Examiner* — Manolis Pahakis
(74) *Attorney, Agent, or Firm* — Buchalter a Professional Corporation

(57) ABSTRACT

A method and system is provided for administering a Repetitive Transcranial Magnetic Stimulation (rTMS) or Transcranial Alternating Current Stimulation (tACS) at a pulse interval of is set equal to the period of a curve that best fits a section of a person's electroencephalogram (EEG) recorded before the pulse train.

20 Claims, 3 Drawing Sheets

EEG CURVE FITTING TO SPECIFY STIMULATION PARAMETER

PRIORITY

This application claims priority to U.S. Provisional Application 62/915,343, filed Oct. 15, 2019; and U.S. Provisional Application 63/021,457, filed May 7, 2020, each of which is incorporated by reference in its entirety herein.

FIELD OF THE INVENTION

The present invention relates to methods to modulate brain activity with repetitive transcranial magnetic stimulation (rTMS) or transcranial Alternating Current Stimulation (tACS) wherein the rTMS or tACS pulse interval is specified as the period of the curve that best fits a section of electroencephalogram (EEG) recorded before the pulse train.

BACKGROUND OF THE INVENTION

Repetitive Transcranial Magnetic Stimulation (rTMS) and transcranial Alternating Current Stimulation (tACS) have been used to improve symptoms of mental disorders and to modify brain function. rTMS uses high energy magnetic pulses from a magnetic field generator that is positioned close to a person's head, so that the magnetic pulses affect a desired treatment region within the brain. tACS uses electric current pulses delivered to the scalp. Traditionally, the pulses are generated at a fixed frequency for a short time duration. For example, a typical rTMS system may generate pulses at 10 Hz for a duration of 6 seconds. A series of pulses generated over a period of time is referred to as a pulse train. An rTMS treatment session may be composed of several pulse trains, with a rest period between each pulse train. A typical rest period may be 55 seconds, such that 5 seconds of rTMS pulses are generated per minute.

The brain's neural oscillations arise from synchronous and coherent electrical activity, and can be recorded using an electroencephalogram (EEG). The intrinsic EEG Frequency of a predefined EEG range is the dominant EEG oscillation within that range. For example, the dominant eyes-closed EEG oscillation in the range of 8-13 Hz is the Intrinsic Alpha Frequency (IAF), or simply the alpha frequency, and can vary between individuals and over time. It has been disclosed by Phillips and Jin (U.S. Pat. No. 8,475,354) that providing magnetic pulses at a frequency that matches a person's IAF can provide an added benefit to the person when compared to rTMS at an arbitrary frequency, such as 10 Hz. In addition, it has been disclosed by Jin (U.S. Pat. No. 9,308,385) that rTMS pulses at a harmonic of a non-EEG biological metric, such as heart rate, that is close to the person's IAF may also provide an added benefit. It is evident that an optimal pulse frequency exists to provide maximum benefit from rTMS for a person.

The dominant frequency of a person's EEG in an EEG band may not match the person's IAF during all time periods. Instead, the dominant frequency tends to drift and vary over time, often changing every few seconds. Therefore, the IAF is instead an average of the dominant frequency over an extended time interval, lasting several seconds or minutes.

SUMMARY

Described herein are methods to treat a person using repetitive transcranial magnetic stimulation (rTMS) or Transcranial Alternating Current Stimulation (tACS). The methods described herein do not require any medication. The methods described herein specify the pulse interval to be equal to the period of the curve that best fits a section of electroencephalogram (EEG) recorded before the pulse train of the stimulation. Exemplary embodiments may include variable and/or constant pulse intervals. A curve may be fit to the EEG signal in different ways. For example, a parametric curve approximation may be used to fit and/or approximate the EEG signal.

In an exemplary embodiment, methods of modulating a brain activity of a person may include subjecting the brain of the person to repetitive current pulses occurring at time intervals which approximately match some time intervals of some local maxima of a parametric curve that approximates a section of an EEG signal of the brain of the person.

In an exemplary embodiment, the repetitive current pulses are created through induction using rTMS. For example, the magnetic field pulses could be generated using a coil external to the head of the person. In another example, the magnetic pulses could be generated using one or more moving permanent magnets external to the head of the person. The magnetic pulse duration could be short or long. The magnetic pulses could be sinusoidal, such that the pulse train resembles a sinusoidal wave.

In an exemplary embodiment, the repetitive current pulses are created transcranially through tACS. For example, the tACS current could be generated through electrodes placed on the person's scalp. The electric pulse duration could be short or long. The pulses could be sinusoidal, such that the electric pulse train resembles a sinusoidal wave.

In another aspect, the fitted curve is a parametric curve defined as a polynomial, which comprises a set of parameters. In another aspect, the parameters comprise the order and coefficients of the polynomial. For example, the polynomial may comprise a single variable, which may be time, where the polynomial solution approximates the EEG amplitude.

In another aspect, the parametric curve is sinusoidal, which comprises a set of parameters. For example, the parameters may comprise frequency, amplitude, and phase. The equation for the curve may comprise a single variable, which may be time, and the equation solution approximates the EEG amplitude.

The section of EEG used for the curve fitting, such as by fitting a parametric curve, may occur at any time. However, the preferred embodiment would have the section of EEG closely precede the pulse train that is administered to a patient. In one aspect, the time period of an EEG signal that is used to determine a parameter of the stimulation (such as a pulse interval) is a time period preceding the administration of the stimulation based on the EEG signal. The stimulation may be rTMS or tACS.

EEG contains energy at a variety of frequencies. However, it may be advantageous to only consider EEG activity with energy contained in a specific frequency band. By filtering the EEG signal, it may be possible to obtain a more accurate curve fitting, allowing for a more consistent and efficacious pulse interval in the pulse train. In one aspect, the EEG has been filtered using a filter with a passband that comprises an EEG frequency band of the brain activity of the person.

It is possible to treat mental disorders effectively using rTMS or tACS at an optimal pulse interval. In some embodiments of at least one aspect described above, the treatment is provided in order to improve symptoms of Autism Spectrum Disorder, Alzheimer's disease, ADHD, schizophrenia, anxiety, depression, coma, Parkinson's disease, substance abuse, bipolar disorder, sleep disorder, eating disorder, tinnitus, traumatic brain injury, post-traumatic stress disorder, or fibromyalgia.

The treatment may also be used to improve various functions of the body. In some embodiments of at least one aspect described above, the treatment is provided in order to improve concentration, sleep, alertness, memory, blood pressure, stress, libido, speech, motor function, physical performance, cognitive function, intelligence, or weight.

BRIEF DESCRIPTION OF THE DRAWINGS

FIG. 1A shows a sample EEG, while

DETAILED DESCRIPTION

Figure 1A:

While certain embodiments or aspects have been provided and described herein, it will be readily apparent to those skilled in the art that such embodiments or aspects are provided by way of example only. It should be understood that various alternatives to the embodiments or aspects described herein may be employed, and are part of the invention described herein.

Described herein are methods for the treatment of a person using rTMS or tACS with an optimal pulse interval. The brain can be thought of as a resonant system, where neurons fire in a synchronous, coherent manner at a resonant frequency. If rTMS or tACS pulses are provided with a pulse interval that is at or near the period of the person's resonant EEG frequency, then the effect of rTMS or tACS may be enhanced, providing additional benefit to the person.

It is generally known that stimulation at a pulse frequency that is close to a person's intrinsic frequency of an EEG band will provide benefit. However, the dominant frequency of EEG may vary significantly over time, often shifting by over 0.5 Hz over the time interval of a few seconds. Therefore, the intrinsic frequency, such as the Intrinsic Alpha Frequency (IAF), is calculated as an average frequency over an extended time interval. This allows the IAF to be more stable and repeatable, but it ignores the transient nature of brain rhythms.

The present invention focuses on the transient variations in brain EEG frequency distribution, allowing a more precise estimate of optimal pulse frequency for the rTMS or tACS device. The present invention uses a relatively short section of EEG, which preferably precedes the pulse train of the rTMS or tACS device. It would be possible to determine an estimate of the intrinsic EEG frequency of a frequency band using a Fast Fourier Transform of the section of EEG and using peak detection to estimate the intrinsic frequency of that section, setting the pulse interval equal to the reciprocal of the intrinsic frequency. In order to determine an intrinsic frequency with a resolution down to 0.05 Hz (the maximum to take advantage of EEG resonance), assuming a sampling rate of 256 Hz (typical EEG sampling rate), the number of points that would be required is (256 Hz)/(0.05 Hz)=5,120. At 256 Hz sample rate, this equates to 20.0 sec of EEG recording. 20 seconds is far too long a time to capture transient changes in the intrinsic EEG frequency. Therefore, an alternate method must be used to provide rTMS or tACS stimulation with a pulse interval that takes advantage of the transient nature of EEG intrinsic frequency.

Although embodiments described herein are generally directed at using exemplary curve fitting to recreate or approximate the EEG signal or partial EEG signal of a patient for determining a pulse frequency to administer stimulation to a patient, such disclosure is not so limited. The exemplary curve fitting may be used in other context or application to analyze the EEG signal and determine a desired parameter to administer the stimulation to a patient. For example, the curve fitting may be used to determine a desired amplitude, and/or desired time location, such as a peak or trough of an EEG signal to administer the stimulation to a patient matching, based upon, or approximating, a characteristics of the EEG section used to generate the wave pattern. In an exemplary embodiment, the fitted curve may be used to determine one or more parameters of the stimulation administered to the patient. For example, the fitted curve may be used to determine, such as by approximation, a frequency, amplitude, and/or phase of the administered stimulation energy. The administered frequency may include a pulse interval, that may be constant and/or variable.

For relatively short EEG sections, instead of detecting the intrinsic frequency using a Fourier Transform or other means, exemplary embodiments may use curve fitting to determine the parameters of a curve that fits the EEG section the best. Then, using the parameters of the fitted curve, the optimal pulse interval for rTMS or tACS can be set. In one exemplary embodiment, methods of modulating a brain activity of a person are provided where the method may include subjecting the brain of the person to repetitive stimulation pulses occurring at time interval(s) which approximately matches some time interval(s) between some local maxima of a parametric curve that approximates a section of an EEG signal of the brain of the person. By measuring the time interval between local maxima of a fitted curve, an estimate of the period of the curve's oscillation, and therefore an estimate of the intrinsic frequency may be found. Alternately, one could equally evaluate the time interval between local minima, or the time interval between zero crossings with identical slope direction (positive or negative). Any of these, or other such measures, would provide the period of oscillation of the fitted curve. The pulse interval of the fitted curve may be a constant pulse interval as an approximate pulse interval between a series of oscillations of the fitted curve approximating a portion of the EEG signal. The pulse interval of the fitted curve may be variable as an approximation of pulse intervals between adjacent, sequential oscillations of the fitted curve approximating a portion of the EEG signal. The pulse interval may be determined from the parameters of the fitted curve.

Stimulation repetitive current pulses may be generated by any device which can impart energy to the brain of a person. In one aspect, the repetitive current pulses are created through induction using rTMS. For example, the magnetic field pulses could be generated using a coil external to the head of the person. In another example, the magnetic pulses could be generated using moving permanent magnets external to the head of the person. The magnetic pulse duration could be short or long. The magnetic pulses could be sinusoidal, such that the pulse train resembles a sinusoidal wave.

In another aspect, the repetitive current pulses are created transcranially through tACS. For example, the tACS current could be generated through electrodes placed on the person's scalp. The electric pulse duration could be short or long. The pulses could be sinusoidal, such that the electric pulse train resembles a sinusoidal wave.

A number of parametric curves may be chosen to fit to the EEG section. It is important, however, that the parametric curve allow for oscillatory behavior to approximate the oscillatory behavior of the EEG section. For example, a simple logarithmic curve is not periodic and is uniformly increasing, so it would not have a measurable oscillatory interval.

One curve that would allow for oscillatory behavior within the EEG band is the polynomial, with the parameters being the order and coefficients of the curve. In one aspect, the parametric curve is a polynomial, which comprises a set of parameters. In another aspect, the parameters comprise the order and coefficients of the polynomial. For example, the polynomial may comprise a single variable, which may be a variable in time, and the polynomial solution would be the approximation of the fitted curve to the EEG amplitude. The equation for a polynomial is given below:

$$E(t) = \sum_{k=0}^{N} a_k t^k$$

where E is the approximation to the EEG amplitude, t is time, and $a_0 \ldots a_N$ are coefficients of the polynomial. A polynomial can approximate a sinusoid in the area of interest, as is shown in a normal Taylor Series expansion:

$$\sin(t) = t - \frac{t^3}{3!} + \frac{t^5}{5!} - \frac{t^7}{7!} + \ldots$$

Therefore, once the order and coefficients are calculated for an exemplary polynomial curve that fits the EEG section by a statistically desired amount, the parameters may be used to estimate the interval between local maxima or minima of the fitted curve.

In another aspect, the parametric curve is sinusoidal, which comprises a set of parameters. For example, the parameters may comprise frequency, amplitude, and phase. The equation for the curve may comprise a single variable, which may be time, and the equation solution may be the approximation to the EEG amplitude of the patient. For example, the curve could have the form:

$$E(t) = A \sin(2\pi f t + \theta)$$

Where E is the approximate EEG amplitude as a function of time t. The parameter A is a scaling factor, f is the frequency in Hz, and θ is the phase in seconds. E(t) is fitted to the EEG section by adjusting the 3 parameters. When complete, the frequency f may be used to find the optimal pulse interval as 1/f.

The curve fitting algorithm may be chosen from a variety of options, which will work with the present invention. For example, a least squares curve fitting algorithm may work well with a linear approximation to the data, and may work with polynomial or sinusoidal curves. This algorithm minimizes the square of the error between the EEG section and the values predicted by the equation. Another example would be nonlinear curve fitting, in which a function is created that, when minimized, gives parameters that best match the EEG section. For example, the Chi Square value represents the sum of the squared error between the EEG section and the calculated fitted curve.

In general, the curve fit algorithm may be iterative, with parameters set to an initial condition, and then varied in order to achieve a minimization of a function which quantifies the closeness of fit for the curve to the EEG data. The initial values may be set to an approximation based on an average brain. For example, a person's alpha frequency is generally between 8 Hz and 13 Hz, with a median of 9.6 Hz. Therefore, this could be used to set initial conditions. Once initial conditions are set, the optimization algorithm may start. Many options are available, such as a derivative-based gradient technique, Newton and quasi-newton methods, a least squares method, or simulated annealing.

The section of EEG used to determine the parametric curve may occur at any time. However, in an exemplary embodiment, the section of EEG that is used for the curve fitting may closely precede the pulse train of the stimulation energy administered to the patient. In one aspect, the section of EEG used to determine the parametric curve is a time period preceding the repetitive current pulse train administered to the subject. Ideally, the EEG section would be short (within 6 seconds or less) and would be relatively noise-free, in order for the dominant rhythm to be present, and would immediately precede the rTMS or tACS pulse train administered to the patient. In an exemplary embodiment, immediately preceding may be that the time interval of the EEG signal used for the curve fitting ends within 15 seconds, within 10 seconds, within 6 seconds, or less of the start of the administration of the stimulation energy. This is because the dominant frequency may vary significantly over a relatively short period of time, so using the section of EEG that immediately precedes the pulse train is most likely to show the dominant frequency that will be most efficacious for therapy. In an exemplary embodiment, the section of EEG signal used to determine the parametric curve may be within a period of time less than or equal to the duration of the section of EEG signal used to determine the parametric curve. For example, the segment of an EEG signal may be six seconds, and the application of a pulse train to the subject may occur within six seconds after the segment of the EEG signal used to determine the parametric curve.

Exemplary embodiments may therefore be used to approximate a period of oscillation of a section of EEG signal. The section of EEG signal used to approximate the period of oscillation may be sufficiently short to capture transient changes in the intrinsic EEG frequency. For example, the section of EEG signal analyzed to approximate the period of oscillation may be less than 15.0 seconds. In some cases, the duration of an EEG signal that is observed and used to approximate the period of oscillation is under 10 seconds, and preferably under 6 seconds. After the termination of the segment of the EEG signal used to determine the period of oscillation, the pulse train may be immediately applied to the subject. In an exemplary embodiment, the application of the pulse train to the subject occurs immediately after the determination of the period of oscillation. The application of the pulse train to the subject may occur within 6 seconds after the termination of the section of EEG signal used to approximately the period of oscillation or to determine the parametric curve.

The initiation of the pulse train may be configured to coincide with an anticipated location of the oscillation of the EEG signal. For example, the system may be configured to track a time the sample EEG signal used for the curve fitting ended. After determining a curve fitting, the curve fitting may be used to determine an oscillation of the EEG signal. The system may then estimate a location of the oscillatory signal, such as a peak, trough, or along the incline or decline of the oscillatory signal. The system may initiated the pulse train to coincide with a desired location along the EEG signal of the patient, after the system measured when the desired location is anticipated. In an exemplary embodiment, the system may be configured to estimate when a peak of the EEG signal may occur and initiate the pulse train such that the peak of the pulse train is anticipated to coincide with the peak of the EEG signal. Any desired location of the EEG signal may be estimated. For example, a time approximate to the peak, just before the peak, at the peak, just after the peak, at a trough, along the incline toward a peak, along the decline toward the trough, and any combination thereof. The targeted location of the EEG signal to coordinate the pulse train may be selected based on the condition to be treated. The targeted location of the EEG signal may be selected based on the EEG signal parameters. The targeted location of the EEG signal may be selected based on a comparison of the EEG signal parameter to a desired EEG signal parameter.

EEG may contain some variability in the oscillations, such as peak interval, amplitude, or other parameter. The variation may not be captured in the approximation from the curve fitting. The system and methods may be configured to introduce variations in the administered EEG signal. For example, the system may be configured to determine an error in the pulse interval. The system may be configured to introduce a similar error in the pulse intervals when administering the pulse train. The system may be configured to shift the pulse interval, such as in hopping the signal with a target frequency based on a frequency of a fitted curve, about a signal range using an error or variability range from the EEG signal or from the EEG signal to the fitted curve. Other variations may also be used, such as a period delay or shortened pulse interval to shift the signal over time. Exemplary embodiments may account for the variability and/or imprecision of the EEG signal and approximation from the curve fitting. Exemplary embodiments may permit the system to detect a second EEG signal to reassess or determine a new fitted curve and update parameters of the pulse train in response thereto.

Exemplary embodiments may use different combinations of analytical features as described herein. For example, the system may be configured to administer based on a peak of the fitted curve, then may switch to the trough, or some other location of the fitted curve. The system may administer session periods on different portions of the fitted curve. The system may similarly combine different delays, errors, approximations, initial conditions, etc. The system may be configured to set these parameters or change the parameters based on the condition to be treated.

EEG contains energy at a variety of frequencies. However, it may be advantageous to only consider EEG activity with energy contained in a specific frequency band. By filtering the EEG signal, it may be possible to obtain a more accurate curve fitting, allowing for a more consistent and efficacious pulse interval in the pulse train. In an exemplary embodiment, the EEG signal used for curve fitting may be filtered using a filter with a passband that comprises an EEG frequency band of the brain activity of the person. For example, much of the rhythmic activity of a person when relaxed with eyes closed occurs in the Alpha band of the EEG. It may be advantageous to filter the EEG section using a bandpass filter, which is designed to pass only the Alpha band, and then to perform the curve fitting algorithm on the filtered EEG signal.

The rTMS or tACS treatment in the present invention may be used in a variety of physiological conditions. In one aspect of the invention, the physiological condition is concentration, sleep, alertness, memory, blood pressure, stress, libido, speech, motor function, physical performance, cognitive function, intelligence, height or weight. The treatment may also be used for a number of neuropsychiatric conditions. In one aspect of the invention, the neuropsychiatric condition is Autism Spectrum Disorder (ASD), Alzheimer's disease, schizophrenia, anxiety, depression, coma, Parkinson's disease, substance abuse, bipolar disorder, sleep disorder, eating disorder, tinnitus, fibromyalgia, Post Traumatic Stress Disorder (PTSD), Traumatic Brain Injury (TBI), memory impairment, pain, addiction, Obsessive Compulsive Disorders (OCD), hypertension, libido dysfunction, motor function abnormalities, small height in young children, stress, obesity, concentration/focus abnormalities, speech abnormalities, intelligence deficits, cognition abnormalities, Attention Deficit Hyperactivity Disorders (ADHD), myalgia, chronic Lyme disease, Rheumatoid Arthritis (RA), autoimmune disease, gout, diabetes, arthritis, trauma rehab, athletic performance, cognitive improvement, or stroke.

Exemplary embodiments may be configured and/or administered based on the condition to be treated. The customization of the treatment administration may be based on the condition to be treated. For example, the selection of setting the pulse interval may be based on the peak, trough, or other location of the fitted curved based on the condition to be treated. For one treatment condition, the peak may be selected, while another treatment condition may use the trough of the signal. Similarly, the start of a pulse train may be configured to correspond with a desired location on the EEG signal based on the condition to be treated. For one treatment condition, the pulse train may be configured to correspond with a peak of the EEG signal of a patient. For another treatment condition, the pulse train may be configured to correspond with a trough of the EEG signal of the patient. The peak and trough are used as examples only, other desired locations on the EEG signal may be used.

The apparatus may include components for generating repetitive magnetic pulses. Exemplary embodiments described herein may include an apparatus for generating repetitive current pulses. The apparatus may be configured to generate the repetitive current pulses through induction using rTMS. For example, the magnetic field pulses could be generated using a coil external to the head of the person. In another example, the magnetic pulses could be generated using moving permanent magnets external to the head of the person. The magnetic pulse duration could be short or long. The magnetic pulses could be sinusoidal, such that the pulse train resembles a sinusoidal wave. The apparatus may also be configured to generate the repetitive current pulses transcranially through tACS. For example, the tACS current could be generated through electrodes placed on the patient's scalp. The electric pulse duration could be short or long. The pulses could be sinusoidal, such that the electric pulse train resembles a sinusoidal wave.

The apparatus may include electrodes for detecting an EEG signal from a patient. The apparatus may include processor and/or memory to record and analyze the EEG signal. In an exemplary embodiment the apparatus may be configured to communicate over a network to a remote processor and/or memory to analyze the EEG signal. The processor(s) and/or memory may therefore be contained within a common housing of the apparatus or may be remote from the leads for detecting the EEG and/or from the components for generating a magnetic pulse train.

In an exemplary embodiment, the memory comprises non-transitory machine-readable instructions that, when executed by the processor(s), is configured to perform the functions described herein. For example, the instructions may include software for fitting a parametric curve to approximate a section of the EEG signal. The instructions may include software for determining a time interval of oscillation of the parametric curve. The instructions may include software for filtering the EEG signal. The system may include hardware and/or software for filtering the EEG signal. The instructions may also be used to control the application of the magnetic pulses, such that the apparatus may be controlled to subject the brain of the subject with repetitive current pulses occurring at the time interval.

Figure 1B:
FIG. 1B shows a possible curve that has been fitted to best match the EEG waveform of FIG. 1A. In addition.
Figure 1C:
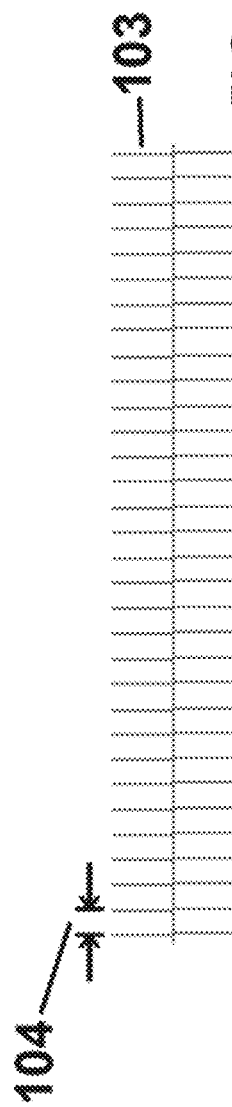
FIG. 1C shows a series of electric pulses with a pulse interval that matches the period of the fitted curve.

FIG. 1B shows an example of a curve fitting with FIG. 1C showing the rTMS or tACS pulse generation. FIG. 1A shows the EEG signal. The EEG signal (101) is rhythmic with a specific period. In this example, a sinusoid curve (102) is fitted to the EEG signal such that the amplitude, frequency, and phase of the fitted curve are selected which minimizes the error difference between the EEG section and the sinusoid. The frequency of the sinusoid may be used to determine the period of the curve, and the interval between pulses (104) of the rTMS or tACS pulse train (103) is set equal to that period. The phase of the fitted sinusoid may also be used to adjust the phase of the pulse train relative to the EEG, so that pulses may be generated at the optimal time relative to the EEG.

Figure 2A:
FIGS. 2A-2C shows a sample sequence of events in which an EEG is recorded (FIG. 2B) and a section of the EEG is used by a curve fitting algorithm to determine a possible curve (FIG. 2C) that has been fitted to best match the EEG waveform in that section. The section immediately precedes the electric pulses (FIG. 2A) having a pulse interval identical to the period of the fitted curve.
Figure 2B:
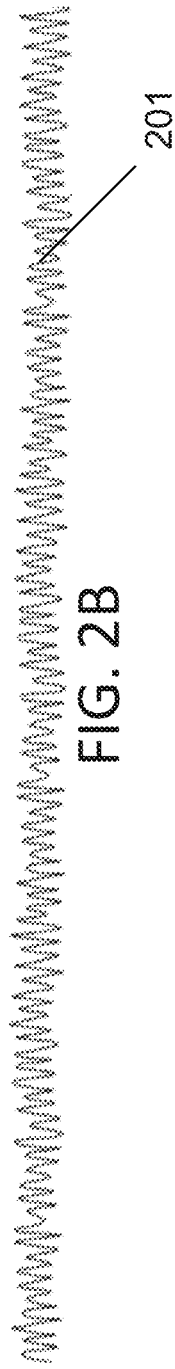
Figure 2C:
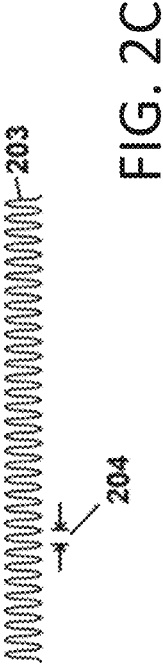

FIG. 2B shows an example plot over time of the EEG signal (201). FIG. 2C shows a sinusoid curve (203) that is fitted to a section of the EEG signal (202) of FIG. 2B. FIG. 2A shows the pulse interval (206) of the rTMS or tACS pulse train (205) that is set equal to the period of the fitted curve (204) for FIG. 2C. As illustrated by the comparison of FIGS. 2A-2C, the pulse train is delivered very soon after the EEG section, and the phase of the pulse train is adjusted to match the phase of the anticipated EEG waveform. Note that in general EEG recording during rTMS or tACS pulse trains is very difficult, and often the curve fitting to such a waveform would likely be unreliable. Therefore, adjustment of pulse interval during a pulse train is generally not preferred.

Figure 3:
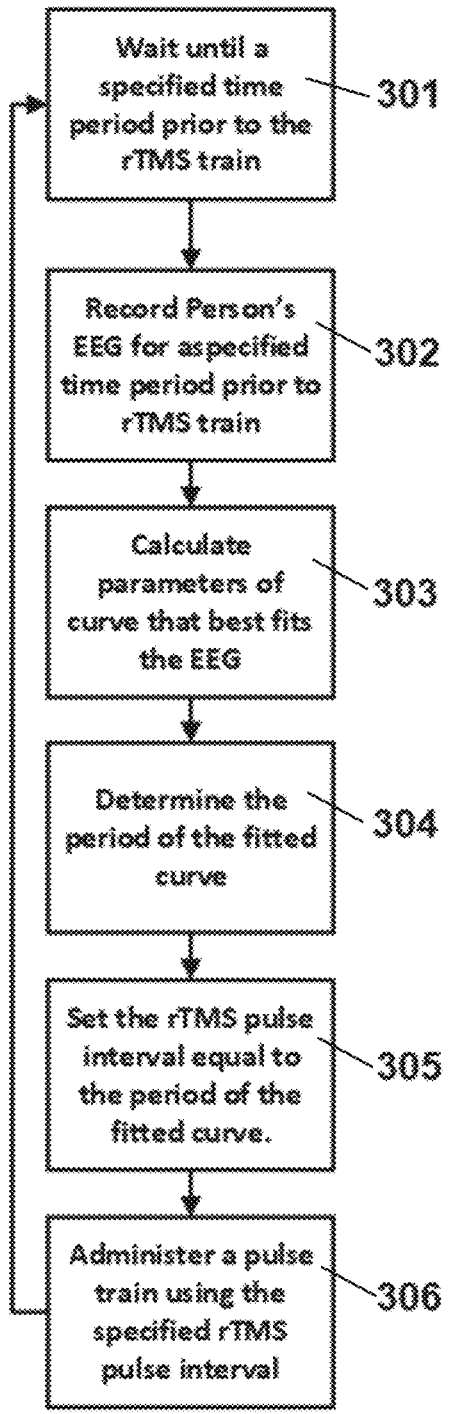
FIG. 3 shows a flowchart of the method of recording EEG, fitting the curve to determine optimal parameters, and delivering a rTMS pulse train with intervals equal to the period of the fitted curve.

FIG. 3 shows the general flow of an exemplary method according to embodiments of the present disclosure. The method may include an optional waiting period. For example, the method may include a step to wait until a specified time period prior to the rTMS or tACS pulse train (301). This time period will preferably be very close to the start of the pulse train. When that time is reached, the person's EEG is recorded (302), generating an EEG section that will be used for curve fitting. A curve type or fitting algorithm is chosen to fit the EEG signal. For example, polynomial or sinusoidal curves may be chosen, and an optimization algorithm is used to find the optimal set of parameters for the curve that best fits the EEG section (303). The period of the fitted curve is determined (304), and the pulse interval of the pulse train is set equal to that period of the fitted curve (305). Then, the pulse train is administered to the brain of the subject (306). After the pulse train, the method can wait until the time period before the next pulse train is set to begin. The method may thereafter be repeated as desired.

"Patient" and "subject" are synonyms, and are used interchangeably. As used herein, they mean any animal (e.g. a mammal on which the inventions described herein may be practiced. Neither the term "subject" nor the term "patient" is limited to an animal under the care of a physician.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the methods or devices are not intended to be exhaustive or to be limited to the precise form disclosed. While specific embodiments of, and examples for, the methods or devices are described herein for illustrative purposes, various equivalent modifications are possible within the scope of the methods or devices, as those skilled in the relevant art will recognize. The teachings of the methods, or devices provided herein can be applied to other processing methods or devices, not only for the methods or devices described.

The elements and acts of the various embodiments described can be combined to provide further embodiments. These and other changes can be made to the device in light of the above detailed description.

In general, in the following claims, the terms used should not be construed to limit the methods or devices to the specific embodiments disclosed in the specification and the claims, but should be construed to include all processing devices that operate under the claims. Accordingly, the methods and devices are not limited by the disclosure, but instead the scopes of the methods or devices are to be determined entirely by the claims.

While certain aspects of the methods or devices are presented below in certain claim forms, the inventor contemplates the various aspects of the methods or devices in any number of claim forms. Accordingly, the inventors reserve the right to add additional claims after filing the application to pursue such additional claim forms for other aspects of the methods or devices.

We claim:

1. A method of modulating activity of a brain of a subject, comprising:
    receiving an EEG signal from a subject during a first time interval, wherein the first time interval is selected to capture a transient change in an intrinsic frequency of the EEG signal;
    fitting a curve to approximate a section of the EEG signal, wherein the fitted curve comprises more than one frequency and the fitted curve approximates the transient change in the intrinsic frequency of the EEG signal;
    determining repetitive pulses using a pulse interval as a period of oscillation of the fitted curve; and
    applying the repetitive pulses to the brain of the subject at the pulse interval for a second time interval, wherein application of the repetitive pulses begins within a third time interval that is less than or equal to the first time interval.

2. The method of claim 1, wherein the fitted curve is a parametric curve and the section of the EEG signal used to fit the parametric curve is less than 10 seconds in duration.

3. The method of claim 1, wherein the repetitive pulses are one or more of magnetic pulses created through induction using repetitive transcranial magnetic stimulation (rTMS) or current pulses created via direct current through transcranial alternating current stimulation (tACS).

4. The method of claim 1, wherein the fitted curve is a polynomial, which comprises a set of parameters.

5. The method of claim 4, wherein the parameters comprise the order and coefficients of the polynomial.

6. The method of claim 1, wherein the fitted curve is sinusoidal, which comprises a set of parameters.

7. The method of claim 6, wherein the parameters comprise frequency, amplitude, and phase.

8. The method of claim 1, further comprising filtering the EEG signal using a filter with a passband that comprises an EEG frequency band of the brain activity of the subject.

9. The method of claim 1, further comprising adjusting a phase of the repetitive pulses to match a location of the EEG signal used to determine the pulse interval.

10. The method of claim 1, further comprising shifting the pulse interval using an error range from the EEG signal.

11. An apparatus for modulating activity of a brain, comprising:
  electrodes operable to receive an EEG signal from a subject for a first time interval, wherein the first time interval is selected to capture a transient change in an intrinsic frequency of the EEG signal;
  one or more processors in communication with one or more memory, wherein the one or more memory includes non-transitory machine-readable instructions that, when executed by the one or more processors, is operable to:
  fit a parametric curve to approximate a section of the EEG signal received from a subject, wherein the parametric curve comprises more than one frequency and the parametric curve approximates the transient change in the intrinsic frequency of the EEG signal;
  determine repetitive pulses using a pulse interval as a period of oscillation of the parametric curve; and
  a generator operable to apply the repetitive pulses at the pulse interval for a second time interval, wherein application of the repetitive pulses occurs within a third time interval that is less than or equal to the first time interval.

12. The apparatus of claim 11, wherein the section of the EEG signal used to fit the parametric curve is less than 10 seconds in duration.

13. The apparatus of claim 11, wherein the repetitive pulses are one or more of magnetic pulses created through induction using repetitive transcranial magnetic stimulation (rTMS) or current pulses created via direct current through transcranial alternating current stimulation (tACS).

14. The apparatus of claim 11, wherein the generator is operable to adjust a phase of the repetitive pulses to match a location of the EEG signal used to determine the pulse interval.

15. The apparatus of claim 11, wherein the generator is operable to shift the pulse interval using an error range from the EEG signal.

16. A method of modulating activity of a brain of a subject, comprising:
  receiving an EEG signal from a subject during a first time interval, wherein the first time interval is selected to capture a transient change in an intrinsic frequency of the EEG signal;
  fitting a curve to approximate a section of the EEG signal, wherein the curve comprises more than one frequency and the curve approximates the transient change in the intrinsic frequency of the EEG signal;
  determining repetitive pulses using a variable pulse interval as an approximation of pulse intervals between adjacent and sequential oscillations of the fitted curve approximating the section of the EEG signal; and
  applying the repetitive pulses to the brain of the subject at the variable pulse interval for a second time interval.

17. The method of claim 16, wherein the fitted curve is a parametric curve and the section of the EEG signal used to fit the parametric curve is less than 10 seconds in duration.

18. The method of claim 16, wherein the repetitive pulses are one or more of magnetic pulses created through induction using repetitive transcranial magnetic stimulation (rTMS) or current pulses created via direct current through transcranial alternating current stimulation (tACS).

19. The method of claim 16, further comprising adjusting a phase of the repetitive pulses to match a location of the EEG signal used to determine the pulse interval.

20. The method of claim 16, further comprising shifting the pulse interval using an error range from the EEG signal.

* * * * *